US007623942B2

United States Patent
Touchstone (10) Patent No.: US 7,623,942 B2
(45) Date of Patent: Nov. 24, 2009

(54) METHOD AND APPARATUS FOR SELECTING NON-OPACIOUS DENTAL MATERIALS

(76) Inventor: C. Alex Touchstone, 14 Honors La., Hattiesburg, MS (US) 39402

( * ) Notice: Subject to any disclaimer, the term of this patent is extended or adjusted under 35 U.S.C. 154(b) by 719 days.

(21) Appl. No.: 11/327,288

(22) Filed: Jan. 6, 2006

(65) Prior Publication Data
US 2006/0177792 A1    Aug. 10, 2006

Related U.S. Application Data

(60) Provisional application No. 60/642,167, filed on Jan. 6, 2005.

(51) Int. Cl.
G06F 19/00    (2006.01)
A61C 19/10    (2006.01)

(52) U.S. Cl. .................. 700/182; 700/97; 700/118; 432/26; 432/226; 600/407

(58) Field of Classification Search .......... 700/97, 700/98, 182; 600/407; 433/26, 196, 223, 433/226
See application file for complete search history.

(56) References Cited

U.S. PATENT DOCUMENTS

| 5,562,448 | A | 10/1996 | Mushabac ............... 433/215 |
| 5,759,030 | A | 6/1998 | Jung et al. ............... 433/29 |
| 5,766,006 | A | 6/1998 | Murljacie ............... 433/26 |
| 5,800,164 | A | 9/1998 | Pfau ............... 433/26 |
| 6,033,222 | A | 3/2000 | Schneider, II et al. .... 433/203.1 |
| 6,328,567 | B1 | 12/2001 | Morris et al. ............... 433/215 |
| 6,358,047 | B2 * | 3/2002 | Lehmann ............... 433/26 |
| 6,499,998 | B2 * | 12/2002 | Kerschbaumer et al. ....... 433/26 |
| 6,568,936 | B2 | 5/2003 | MacDougald et al. ....... 433/223 |
| 6,743,014 | B2 | 6/2004 | Kerschbaumer et al. ....... 433/26 |
| 6,882,894 | B2 | 4/2005 | Durbin et al. ............... 700/118 |
| 7,463,942 | B2 * | 12/2008 | O'Brien et al. ............ 700/118 |
| 2001/0049082 | A1 * | 12/2001 | Kerschbaumer et al. ....... 433/26 |
| 2002/0081547 | A1 | 6/2002 | Kerschbaumer et al. |

(Continued)

FOREIGN PATENT DOCUMENTS

EP    1 252 867    10/2002

OTHER PUBLICATIONS

International Publication No. WO 2004/0098378 A2, published Nov. 18, 2004, to Orametrix, Inc.

(Continued)

*Primary Examiner*—Ramesh Patel
*Assistant Examiner*—Douglas S Lee
(74) *Attorney, Agent, or Firm*—Waddey & Patterson; Edward D. Lanquist, Jr.

(57) ABSTRACT

A method and system for selecting dental constructions using translucent materials that match an individual's preexisting tooth appearance uses a set of reference templates. The reference templates are constructed from layers of various translucent dental materials positioned on bases constructed from actual or simulated tooth structures. The layers of translucent materials have a thickness that varies in increments that correspond to the likely thicknesses of the materials when used in dental constructions. A reference table is created based upon color measurements of each of the reference templates. A color measurement of the individual's preexisting teeth is then compared to the reference table to determine which particular dental construction will most closely match the individuals preexisting teeth.

20 Claims, 3 Drawing Sheets

U.S. PATENT DOCUMENTS

| | | | |
|---|---|---|---|
| 2003/0124481 A1 | 7/2003 | Zun | |
| 2003/0190578 A1* | 10/2003 | Lehmann | 433/26 |
| 2004/0067465 A1 | 4/2004 | Schomann | |
| 2005/0089822 A1 | 4/2005 | Geng | 433/215 |
| 2005/0283065 A1* | 12/2005 | Babayoff | 600/407 |
| 2008/0090197 A1 | 4/2008 | Touchstone | |

OTHER PUBLICATIONS

International Publication No. 2005/072227 A2, published Aug. 11, 2005, to Gerber Scientific Products, Inc.

International Publication No. WO 2006/031096 A1, published Mar. 23, 2006, to Oratio B.V.

European Patent Office Search Report dated May 15, 2008 for PCT/US2006000453.

Co-Pending U.S. Appl. No. 11/159,795, filed Jun. 23, 2005, by C. Alex Touchstone.

* cited by examiner

METHOD AND APPARATUS FOR SELECTING NON-OPACIOUS DENTAL MATERIALS

CROSS-REFERENCES TO RELATED APPLICATIONS

This application is a Non-Provisional Utility application which claims benefit of co-pending U.S. Patent Application Ser. No. 60/642,167 filed Jan. 6, 2005, entitled "Method and Apparatus for Determining the Dental Material(s) that Will Result in the Correct Final Color of a Non-Opacious Dental Restoration by Measuring and Predicting the Influence of the Color of Prepared Teeth on the Final Color", co-pending U.S. patent application Ser. No. 11/159,795 filed Jun. 23, 2005, entitled "Method and Apparatus for Selecting Non-Opacious Dental Materials" and co-pending PCT Patent Application Serial No. PCT/US2005/023024 filed Jun. 29, 2005, entitled "Method and Apparatus for Selecting Non-Opacious Dental Materials" which are hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

FIELD OF THE INVENTION

The present invention is generally directed toward the field of dental reconstructions. More particularly, the present invention is directed toward a method and apparatus for the selection of a dental restoration that uses a non-opacious material such that the final dental restoration will match the color and appearance of an individual's teeth.

BACKGROUND OF THE INVENTION

The present invention relates to a shade or color determination apparatus and method for dental restorations where translucent materials are used that account for the influence of underlying tooth structure on the final shade of the dental restorations when an opaque layer of dental material is not used in the fabrication of the dental restoration.

A shade determination apparatus and method is known from U.S. Pat. No. 6,499,998 which discloses a method for specifying and determining appropriate colors for teeth and dental restorations in accordance with a set of reference templates. A shade guide such as disclosed in the '998 patent has a plurality of color groups, wherein each group is representative of a tooth with a certain brightness, saturation and/or hue and, thus, is assigned a certain shade. Each individual shade in a shade guide is termed a shade tab and is typically fabricated to resemble the shape of an upper incisor tooth with a material structure of one to as many as five or more layers of material.

A shade guide is limited in its effectiveness as a shade determination device. First, commercial shade guides have a limited number of shade tabs. Moreover, the user's ability to discern one shade from another is often compromised by the user's inability to discern small color differences due to eye strain, non-standard lighting conditions or by problems with the user's anatomy related to color discrimination.

Additional problems arise in achieving an accurate shade match using a commercial shade guide due to differences in the physical and, thus, light refractive properties of the materials used to manufacture the shade guides themselves versus the materials used to fabricate dental restorations.

While systems similar to that described in the aforementioned U.S. Pat. No 6,499,998 aim to overcome many of the limitations inherent in the use of commercial shade guides, they fail to address the influence of the color of the underlying tooth structure on the final shade of a dental restoration when translucent dental materials are used without an opaque layer to mask out the internal structure's influence.

Until recently, the use of an opaque layer in the fabrication of dental restorations was the norm. However, with the introduction and increasing use of more durable translucent dental ceramics in the fabrication of dental restorations, an opaque core material is often no longer employed. Because these ceramic restorations have no opaque core, the final color of the restoration is influenced by the color, or shade, of the prepped tooth that underlies and supports the restoration itself. However, the prior art, including U.S. Pat. No. 6,499,998, fails to take into account the significant influence of the underlying tooth structure. The present application addresses this key issue in a novel and commercially viable manner.

BRIEF SUMMARY OF THE INVENTION

An object of the present invention is therefore to provide a dental material(s) and/or shade selection apparatus that will measure, predict and accurately account for the influence of the underlying prepared tooth on the final shade of a dental restoration when layer(s) of translucent dental materials are used without an opaque masking layer thereby significantly improving shade matching in such circumstances.

This object is achieved in accordance with the apparatus and method of the present invention. In particular, a dental CAD/CAM system constructed in accordance with an embodiment of the present invention includes a three dimensional measuring camera for measuring a three-dimensional shape of a basic dental structure. A construction unit constructs a dental restoration body for application to the basic dental structure. The construction unit calculates a thickness of the restoration body for at least at one area that is representative of an appearance of the restoration body applied on the basic dental structure. A measuring camera, which may be the three-dimensional measuring camera, with an optical sensor, such as an image detecting sensor, measures the relevant optical properties of the basic dental structure and the desired appearance of the dental restoration body. A first data storage area stores reference data of relevant optical properties of different translucent dental materials. A second data storage area stores data concerning a dependency between relevant optical properties of the basic dental structure, values of the relevant optical properties of the desired appearance, the thickness of the restoration body and relevant optical properties of the translucent dental materials. An interface receives target values of the desired appearance of the restoration body, the optical properties of the basic dental structure and the thickness of the restoration. A calculation unit determines an appropriate translucent dental material for use in the dental restoration body based upon the reference data and the dependency.

Another embodiment of the present invention is directed toward a method of producing a dental restoration body for application to a basic dental structure such as a prepared tooth. The dental restoration body may be any type of dental restoration such as an inlay, an onlay, a crown or a veneer. The restoration body is made of a translucent dental material and the method is part of a CAD/CAM-process. In accordance with the method, a dataset concerning the dental restoration body for application to the basic dental structure using computer aided design methods is provided. Reference data concerning relevant optical properties of different translucent dental materials and a dependency between relevant optical properties of the basic dental structure and the translucent dental materials, target values for desired optical properties of the dental restoration body to be produced, a thickness of the restoration body and the relevant optical properties of the translucent dental material is also provided. The dependency may be a functional dependency or an empirical known dependency. The relevant optical properties of the different translucent dental materials may include different color or translucency values. The relevant optical properties of the basic dental structure are then determined. A target value corresponding to the desired optical properties of the restoration body when applied to the basic dental structure to be produced is determined. The target value may be a color or translucency value that is selected based upon optical properties of teeth adjacent of the basic dental structure. A thickness of the dental restoration body to be produced on at least one area of the basic dental structure which is relevant for the appearance of the dental restoration body is determined. A dental material is selected for the dental restoration body based upon the reference data and the dependency between the optical properties of the basic dental structure and the translucent dental materials.

Yet another embodiment of the present invention is directed toward a computer program for determining an appropriate translucent dental material or construction for use in producing a dental restoration for use with an existing dental structure. The computer program includes a data base containing optical properties of different translucent dental materials or constructions and a dependency between optical properties of the dental restoration, the existing dental structure and the translucent dental material or construction. An input routine receives information concerning a desired optical property, such as a color or translucency value, and the thickness of the dental structure to be produced. The desired optical property maybe based upon an optical property of teeth adjacent the existing dental structure. A selection routine determines an appropriate dental material or construction for use in producing the dental restoration based upon a relationship between the desired optical property and thickness of the dental restoration, the optical properties of the existing dental structure and the translucent dental material or construction. The relationship is preferably a functional dependency or an empirical known dependency contained in a look-up table. The computer program may be incorporated in a shade determination device or a dental CAD/CAM system.

The inventive measures described herein make it possible for the first time to accurately select translucent dental materials that will result in adequate final coloration of the dental restoration even though no opaque masking layer is employed. This is based particularly on the fact that reference data is used that corresponds to the materials used, the underlying tooth structures and to the order in which they are layered and to the thickness of each layer as well as the average thickness of the restoration to be fabricated. The comparison apparatus and method result in more precise, consistent color matching of the final dental restoration to that of the desired color than in any previous method that uses translucent dental materials that do not include an opaque masking layer.

In accordance with the invention, it is advantageous use reference data derived from simulated and/or natural tooth templates that include colors that correspond to the colors of teeth found in nature and to known dental color systems. Likewise, it is particularly advantageous for the dental material data to correspond in thickness and/or layering order to the thicknesses and layering orders that are commonly employed in the fabrication of dental restorations. The dental material data will therefore correspond to dental materials having varying thicknesses that are combined with one another in varying combinations that are representative of those commonly employed in practice.

In accordance with the invention, it is also advantageous to arrive at the appropriate materials to be used through an automated process. The relevant data is therefore displayed on a commonly available computer screen along with patient data information. The data may be converted to a printed format. In accordance with the invention, it is particularly advantageous for the data generated to be presented on the screen in one or more formats, including but not limited to numerical values, mapping of the coloration of the planned dental restoration overlaid on an outline of a tooth, alternate materials selections and their impact on the color match, user selectable color matching tolerance ranges and warnings when the tolerance ranges have been exceeded.

In accordance with the invention, it is advantageous for a variety of custom color matching algorithms to be user selectable, giving the user the option to increase or decrease the weight of individual parameters in the determination of an acceptable color match. The relative weight of parameters of material thickness, region of the tooth considered, material type(s), material layering order, variation of the overall or regional color of the prepped tooth, and predicted final dental restoration color, as well as any other parameter that is a part of the color matching formula employed, are all user adjustable. Thus, the present invention allows the user to custom tailor the functionality of the device to suit individual color matching needs.

BRIEF DESCRIPTION OF THE SEVERAL VIEWS OF THE DRAWINGS

Additional advantages, features and details of the invention result from the following description of exemplary embodiments with the aid of the accompanying drawings, in which.

DETAILED DESCRIPTION OF THE INVENTION

The present invention is directed toward an apparatus and method for measuring the influence of prepared or reduced teeth, also referred to herein as underlying tooth structure, on the final shade of a dental restoration when translucent dental materials are used without an opaque layer. In accordance with the invention, a set of reference templates are layered over simulated or actual teeth, whereby instrumental measurements of the coloration of sandwiches of teeth and templates can be determined. The templates and teeth are arranged in a layered arrangement that corresponds to the order in which they are found in commonly used dental restorations, taking into account layer thickness, materials used and preparation and/or manufacturing methods commonly employed. The colorations of the actual or simulated teeth and the colorations of the templates are measured separately.

The coloration data of both the layered sandwiches of templates and simulated or actual teeth and of the simulated or actual teeth themselves and of the templates themselves are stored in a storage apparatus for comparison purposes. The influence of the simulated or actual tooth on a given material combination is determined by mathematical comparison of the coloration of the simulated or actual teeth alone versus the combination of material template layer(s) and the simulated or actual teeth. Likewise, the desired coloration or final shade is entered into the storage apparatus and the combination(s) of materials that result in the desired final shade are proposed based on mathematical comparisons.

Figure 1:
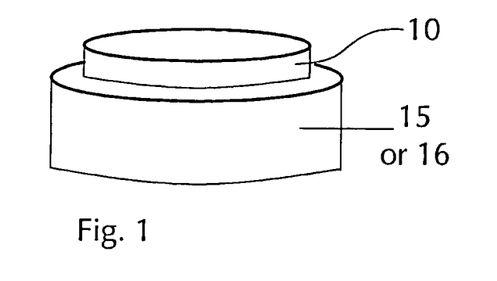
FIG. 1 is a perspective side elevation of the first combination of layered reference templates.
Figure 6:
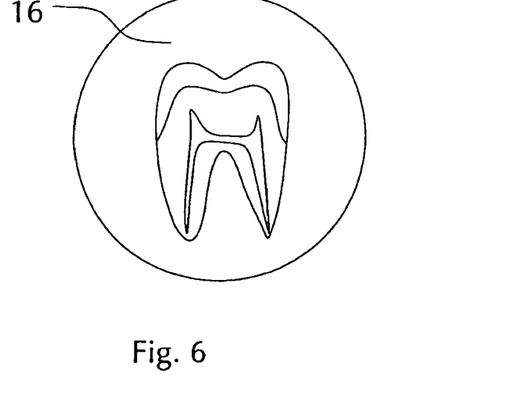
FIG. 6 is a plan view of the template of a cross section of natural tooth structure embedded in a fixation medium.

Referring now to FIG. 1, an exemplary illustration of an embodiment of a plurality of similar reference templates comprised of a plurality of material layers including at least one translucent dental material layer and at least one underlying layer of simulated or actual tooth structure is shown. The combination reference template illustrated in this exemplary embodiment represents a monochromatic dental restoration that does not contain an opaque layer. Material layer 10 is preferably formed as a circular wafer of dental material at a certain known thickness and diameter. The method used to form the material is one of many common to the industry and corresponds to the methods that are to be employed in the fabrication of the actual dental restorations to be used. Material layer 15 is formed from either simulated or natural tooth structure. In the case of layers formed of natural tooth structure, the tooth specimen is either encased in a fixation medium and sectioned as illustrated in FIG. 6, or is formed from natural cellular material through a synthetic growth method, the details of which are outside the scope of the present invention. Although this exemplary embodiment illustrates circular layers, any shape that is conducive to the color measurement procedures may be employed. To better illustrate the layers of the reference template and their corresponding order, the wafer thicknesses shown in the figures are not necessarily drawn to scale.

A plurality of circular wafers 12 mm in diameter of the same dental material and the same color are manufactured at thicknesses ranging from 0.2 mm to 2.0 mm in 0.1 mm increments. The diameter of 12 mm is generally preferable although not an absolute requirement. Adjustments in this dimension may be made to accommodate for the particular requirements related to the sample size accepted by the measurement instrumentation used. Similarly, a plurality of wafers made from each color of each dental material to be considered for use in the dental procedures are manufactured at thicknesses ranging from 0.2 mm to 2.0 mm in 0.1 mm increments.

Figure 5:
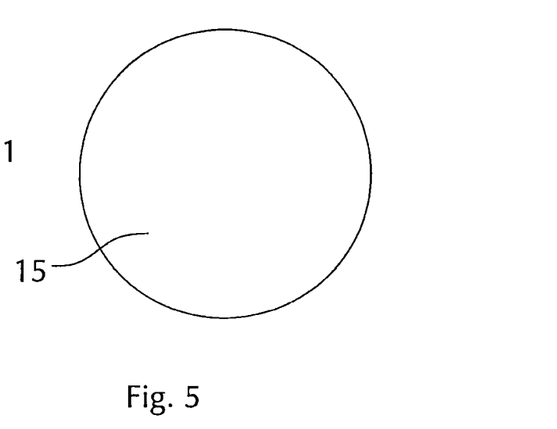
FIG. 5 is a plan view of the template of simulated tooth structure or of synthetically-grown natural tooth structure.

A plurality of wafers of material that simulate the optical characteristics of natural tooth structures is manufactured using known methods the details of which are outside the scope of this invention. The plurality of created wafers is representative of the range of colors of enamel and/or dentinal tooth structures found in nature. At a minimum, reference wafers are produced in different colorations which match the colors of the 24 colorations most commonly found in nature. These wafers are preferably 18 mm in diameter and 15 mm thick or, at a minimum, a thickness and diameter which are in excess of that required by the color measurement instrumentation to minimize edge loss or light scattering errors. However, it will be readily appreciated by those skilled in the art that adjustments in the diameter of the wafers may be made to accommodate for the particular requirements related to sample size accepted by the measurement instrumentation used. FIG. 5 illustrates an exemplary embodiment of a wafer template 15 of simulated or synthetically-grown natural tooth structure.

Alternately, a plurality of wafers of natural tooth structure may be fabricated by embedding actual human, bovine or other animal teeth in a fixative medium and sectioned at a location that is representative of the area of the tooth that is to be used for reference measurements. The thickness of the sectioned wafers is preferably 15 mm or, at a minimum, in excess of that required by the color measurement instrumentation to minimize edge loss or light scattering errors. The diameter of the plurality of sectioned tooth structure wafers is 18 mm. As set forth above, adjustments in this dimension may be made to accommodate for the particular requirements related to sample size accepted by the measurement instrumentation used. A plurality of wafers of the natural tooth structures are created that are representative of the range of colors of enamel and/or dentinal tooth structure found in nature. At a minimum, reference wafers are produced in different colorations which match the colors of the 24 colorations most commonly found in nature. FIG. 6 illustrates an exemplary embodiment of a wafer 16 constructed from a natural tooth structure.

The assembled reference template illustrated in FIG. 1 includes one monochromatic dental material, wafer 10, centered over and adjacent to either simulated or actual tooth structure, illustrated as either wafer 15 or 16. The two layers are coupled to one another in a temporary fashion by means of a liquid, optically-transparent coupling medium. The aforementioned method of temporary coupling allows for a plurality of combinations of materials and tooth structures to be created and measured without the need for any unnecessary duplication of wafer samples.

Figure 2:
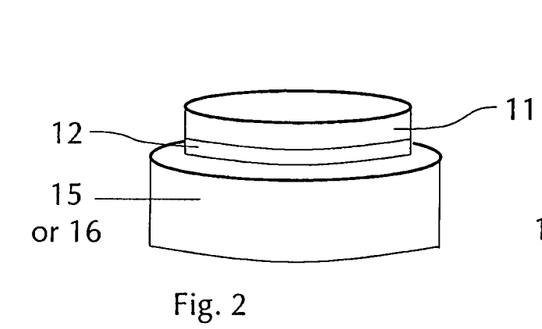
FIG. 2 is a perspective side elevation of the second combination of layered reference templates.

FIG. 2 illustrates an exemplary embodiment of a modified reference template wherein two layers, wafers 11 and 12 of dental restorative material and one layer, 15 or 16, of simulated or actual tooth structure are employed. In this instance, wafer 11 is a simple enamel layer of the planned dental restoration and layer 12 is the dentinal layer. The combination reference template that is formed in this exemplary embodiment represents a simple polychromatic dental restoration that does not contain an opaque layer. The enamel and dentinal reference wafers are manufactured in a manner which is generally known and corresponds to the methods to be used in the actual fabrication of dental restorations. A plurality of circular wafers 12 mm in diameter of the same dental material and the same color are manufactured at thicknesses ranging from 0.2 mm to 2.0 mm in 0.1 mm increments. The diameter of 12 mm is generally preferable although not a requirement. Adjustments in this dimension may be made to accommodate for the particular requirements related to sample size accepted by the measurement instrumentation used. Similarly, a plurality of wafers made from each color of each dental material to be considered are manufactured at thicknesses ranging from 0.2 mm to 2.0 mm in 0.1 mm increments.

In the exemplary embodiment illustrated in FIG. 2, the assembled reference template illustrated includes a dentinal dental material, wafer 12, centered over and adjacent to either simulated or actual tooth structure, illustrated as either wafer 15 or 16. The two layers are coupled to one another in a temporary fashion by means of a liquid, optically-transparent coupling medium. Next, a wafer of enamel dental material, wafer 11, is placed adjacent to and centered over the dentinal dental material, wafer 12 and coupled by means of the coupling medium. The combination reference template that is formed in the exemplary embodiment in FIG. 2 represents a two-layer, polychromatic dental restoration that does not contain an opaque layer.

Figure 3:
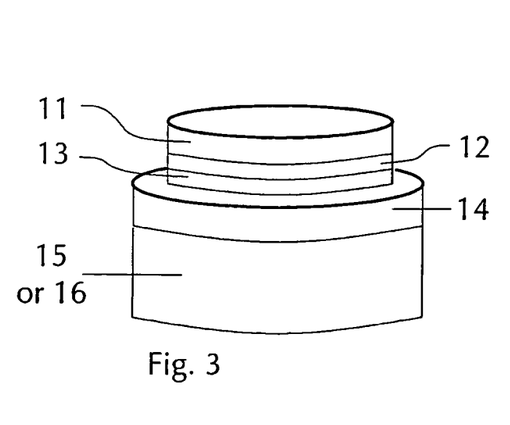
FIG. 3 is a perspective side elevation of the third combination of layered reference templates.

FIG. 3 illustrates an exemplary embodiment of a modified reference template wherein three layers, wafers 11, 12, and 13 of dental restorative material and two layers, wafer 14 and wafer 15 or 16, of simulated or natural tooth structure are combined to form the reference template. In the exemplary embodiment illustrated in FIG. 3, each dental restorative material wafer corresponds to a plurality of materials that are commonly used in the fabrication of dental restorations. For example, wafer 11 may be a simple enamel layer of the planned dental restoration, layer 12 the dentinal layer and layer 13 the deep dentinal or color modifying layer. The remaining two layers, wafer 14 and wafer 15 or 16 are both made in the aforementioned manner from either actual or simulated tooth structure. In the exemplary embodiment illustrated in FIG. 3, wafer 14 is made of either natural or synthetic enamel tooth material and wafer 15 or 16 is either natural or synthetic dentinal tooth material.

The combined reference template illustrated in FIG. 3 is constructed as in the aforementioned exemplary embodiments illustrated in FIG. 1 and FIG. 2 by arranging each layer in the order illustrated and coupling the layers to one another with an optically transparent liquid coupling medium. The combination reference template that is formed represents a more complex polychromatic dental restoration that does not contain an opaque layer. The thickness of each dental material layer corresponds to one of a plurality of thicknesses that are commonly employed in the layering of dental restorations, ranging from 0.2 mm to 2.0 mm. As in the other two embodiments, the diameter of the dental material wafers is generally selected to be 12 mm or a width that is conducive to measurement using commonly available instruments. Additionally, as in the other two previously discussed exemplary embodiments, a plurality of templates are constructed that contain a plurality of wafers of different thicknesses and colors representative of the various combinations that are commonly employed in the construction of actual dental restorations.

While the exemplary embodiments that are described herein are representative of the common order and level of layering complexity of dental restorations, it is obvious that the number of dental material wafer layers may be increased further to represent any arrangement of dental materials that may be employed either now or in the future and that the individual thicknesses and physical properties of the materials may also be varied according to current or future known manufacturing methods.

Figure 4:
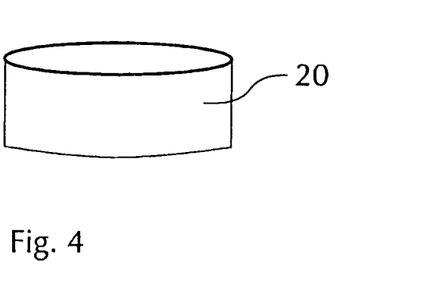
FIG. 4 is a perspective side elevation of a single layer of template material.

FIG. 4 illustrates an exemplary embodiment of a wafer, 20, of dental restorative material that is sufficiently thick in and of itself to facilitate accurate color analysis without induction of edge loss errors. The thickness of each material will vary according to that material's relative translucency in order to meet the aforementioned requirement. The wafers are analyzed using a known color measurement method such as a spectrophotometer or colorimeter.

It is obvious that the instrument used for analysis is preferably the same as that to be employed in the color measurement in the planning of the restoration of the patient's teeth. When this is not practical, the coloration of the patient's teeth can be determined by another means and input separately into the device for comparison and material matching purposes.

A measurement of the coloration of each material is made using a known color measurement instrument selected for generating the reference data. The data is stored in a computer database for analysis and comparison to other data collected as described herein. Next, the wafers 15 or 16 of synthetic or natural tooth structure are analyzed for their individual colorations using the same instrumentation. The coloration data generated are cataloged and stored in the computer database. Likewise, the various combined layers of wafers 14 and 15 or 16 are measured with the same instrumentation and the data is stored for later use. Data generated from the color measurements are stored in the storage apparatus along with the template layering order, wafer thickness(es) and other pertinent data.

The coloration of the combined reference templates illustrated as exemplary embodiments in FIG. 1, FIG. 2 and FIG. 3 is preferably analyzed with the same color measurement instrument as the individual's existing teeth such that variations due to the use of different equipment is minimized. The coloration data along with layering order, wafer thickness(es) and other pertinent cataloging information are stored in the storage apparatus. All logical combinations of layering of wafers of dental materials along with the coloration of synthetic or natural tooth structure are measured and the data recorded and assigned to its corresponding combined reference template.

All relevant combinations of materials are measured, totaling 1000 or more depending on the variety of materials considered for matching purposes. While it is obvious that the initial template preparation and data collection is somewhat laborious, the process has great advantage in that the data are collected one time and can then be used for any number of shade matching events as long as the same or optically similar dental materials are used in the actual fabrication of the planned dental restorations.

Once the coloration data has been gathered for all likely combinations of materials and tooth structure, the system is ready for use and can be made functional by one of several methods without deviating from the scope of the invention.

In one embodiment, the data are stored in a subprogram of an identical color measurement instrument to that which was used to gather the coloration data of the reference templates themselves. The end user, most commonly either a dentist or dental lab technician, simply uses the color measurement device to measure the coloration of the prepared tooth that is to be restored and the desired shade derived from measuring adjacent teeth. Alternatively, the desired shade of the planned dental restoration may be determined by the user by making a visual comparison using a commercially available shade guide and the desired shade of the restoration entered manually by the user. The user then manually enters the average thickness of the planned restoration. The thickness measurement can be made by one of several methods the details of which are outside the scope of the present invention. Then, the subprogram runs a series of color difference calculations and arrives at the best fit of dental materials which result in the smallest color difference between various materials combinations and the desired final shade, taking into account the measurement of the shade of the prepared tooth.

In a further embodiment, the data generated during the setup phase are stored in a stand-alone commercially available computer. The computer includes a data base containing optical properties of different translucent dental materials or constructions and a dependency between optical properties of the dental restoration, the existing dental structure and the translucent dental material or construction. An input routine receives user input information concerning a desired optical property and thickness of the dental structure to be produced. A selection routine then determines an appropriate dental material or construction for use in producing the dental restoration based upon a relationship between the desired optical property and thickness of the dental restoration, the optical properties of the existing dental structure and said translucent dental material or construction. The desired optical property may be a color value or translucency value and may be based upon an optical property of adjacent teeth of the existing dental structure. Thus, an embodiment of the present invention implemented in a standard PC prompts the user to manually enter the prepared tooth shade, the desired shade and the average thickness of the planned restoration. Then, using the data provided by the user, the computer performs color difference calculations to arrive at a proposal of materials that will result in the smallest color difference.

In a third embodiment, the reference template data generated are stored in a subprogram of a CAD/CAM dental restoration manufacturing unit. During the design phase of fabrication, the CAD/CAM machine automatically calculates the average thickness of the planned restoration and delivers the data to the subprogram; the user manually enters the desired final shade and the prepared tooth shade. The subprogram makes the appropriate color difference analyses and proposes the materials that will result in the closest shade match.

In a fourth embodiment, a color measurement instrument and the CAD/CAM dental restoration unit are linked to one another, either physically or wirelessly or by virtue of some other known communication method and the data generated are stored in a subprogram in either unit. The prepared tooth shade is measured with the color measurement device, the planned restoration average thickness is calculated by the CAD/CAM software, and the desired shade of the restoration is entered manually by the user or is determined by measurement of an adjacent tooth with the color measurement device. As in the other exemplary embodiments, the subprogram calculates the materials combination that results in the best shade match.

It is obvious that a number of other variations in the functionality of the method are possible without deviation from the scope of the invention. For instance, the program can be given a color difference tolerance range that will function to warn the user when this parameter is exceeded. Further, materials to be employed can be entered by the user and an estimate of the resultant shade of the restoration can be calculated. The program can also propose more than one combination of materials to arrive at the desired shade and present the color difference values for each combination, allowing the user to make the selection he or she deems appropriate.

In a further exemplary embodiment, the apparatus may take the form of a manual computing device such as a wheel wherein all but one variable is input and the solution to the remaining variable is read by the user.

It is also obvious that measurements of the color modifying layers of material can be included in the reference data. The color modifiers may take the form of surface stains or glazes on the dental materials themselves or that of layers of resin bonding agents that have physical properties such that they have an influence on the final coloration of the planned restoration. The data generated in these instances will then be used to provide additional material combinations and/or solutions to color matching problems.

The target area of the tooth for color matching may also be selected to suit the needs of the user. For instance, the middle one third of the labial surface of the tooth may be selected as the target area for anterior teeth whereas the occlusal surface might be considered preferable for posterior teeth. The average thickness and/or coloration measurements in the target area only will then be considered in the materials selection or color matching calculations.

Figure 7:
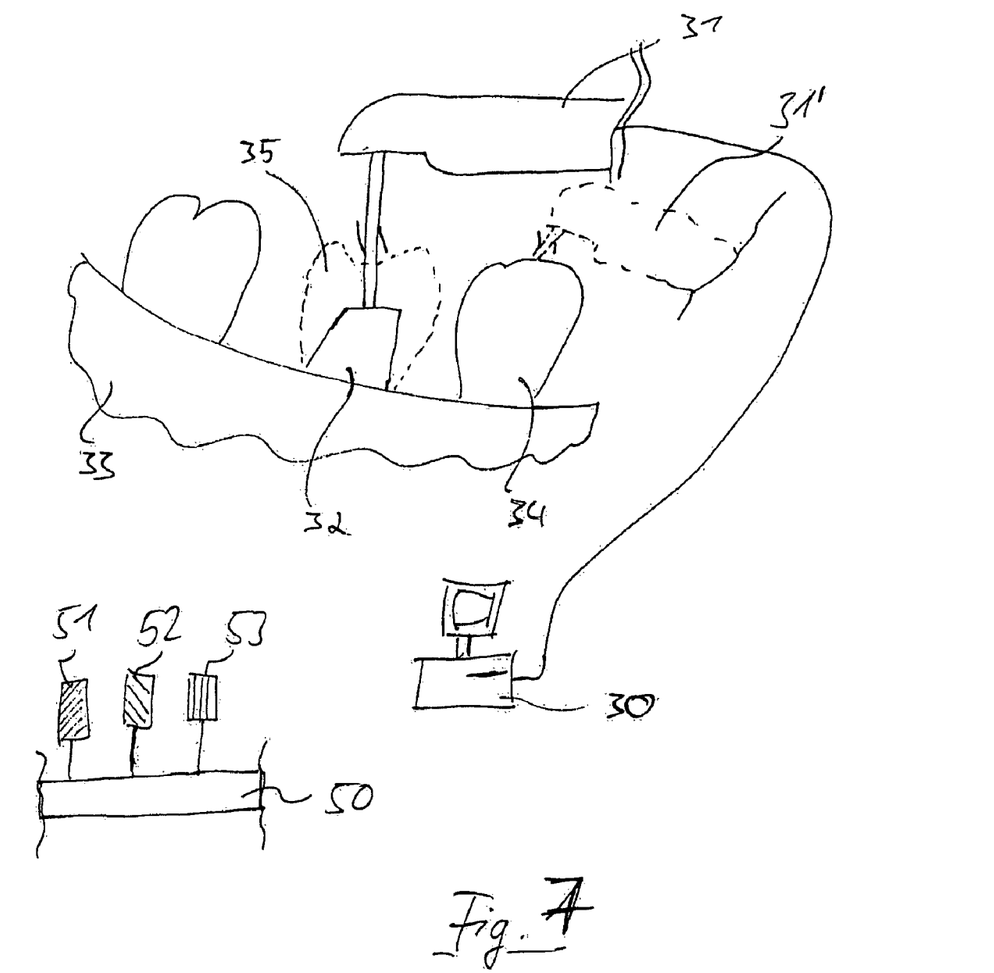
FIG. 7 is a schematic view of a CAD/CAM system with a measuring camera measuring a prepared tooth.

Referring now to FIG. 7, a CAD/CAM system is shown, which includes a construction unit 30. The construction unit 30 is basically a computer comprising a processor, at least one storage area, an input device and display means. The CAD/CAM system also includes a measuring camera 31 which is connected to the construction unit 30. The measuring camera 31 transfers data from the camera 31 to the construction unit 30. In a first position, the measuring camera 31 measures optical properties of a basic dental structure 32. The basic dental structure 32 could be a prepared tooth as well as an abutment of an implant or any other structure known in dentistry for building an artificial tooth. The basic dental structure 32 is preferably fixed to the jaw 33 of patient at the time the measurements are taken.

The measuring camera 31 may simply be a camera for taking color measurements or a three-dimensional measuring camera which is able to measure three-dimensional data concerning tooth structure as well as color. In the second case, the camera 31 may be equipped with an appropriate sensor for both tasks or may have a special sensor for measuring the optical properties. If a three dimensional camera is utilized, the measuring camera 31 will also measure the three-dimensional shape of the basic structure 32 in the first position. Additional three-dimensional data concerning the adjacent tooth 34, the shape of the gingiva and the shape of the opposed tooth may also be measured. The camera 31 is moved to the appropriate position, shown with dotted lines 31', to gather additional data such as the optical properties of an adjacent tooth 34. If a three-dimensional measuring camera 31 is not used, a separate camera for three-dimensional measurements (not shown) may be connected to the construction unit 30 for obtaining the three-dimensional data which is necessary for the construction of the restoration body 35. The restoration body 35 to be constructed, which in FIG. 7 is shown as a crown 35, is represented by dotted lines. While a crown 35 is shown for exemplary purposes, it will be appreciated by those skilled in the art that other restoration bodies, such as inlays, onlays, veneers and the like, can be constructed.

The CAD/CAM system acquires data concerning relevant optical properties of the basic dental structure 32 and the adjacent tooth 33 with the camera 31 and stores this data in the storage area of the construction unit 30. Data concerning the shape of the basic dental structure 32 and the optionally acquired three dimensional measurement data of the basic dental structure's surroundings may also be stored in the storage area. In one embodiment of the invention, the relevant optical properties measured are solely properties concerning the color of the objects to be measured. However, in alternative embodiment translucency values are also included.

A carrier 50 is used to contain blanks 51-53 of dental materials with different colors and/or translucencies. The designed restoration body 35 is constructed from one of the blanks 51-53. The blank 51-53 to be used is selected based upon the data gathered from the camera 31 and the desired final appearance of the restoration body 35. The construction unit 30 shown in FIG. 7 is used to construct a dataset corresponding to the desired shape of the restoration body 35 to be manufactured. The construction unit 30 uses the three dimensional data related to the outer shape of the basic structure 32 to create this dataset. The formation of dental constructions using computer aided design principles is well known in the art and will not be discussed greater detail herein.

Figure 8:
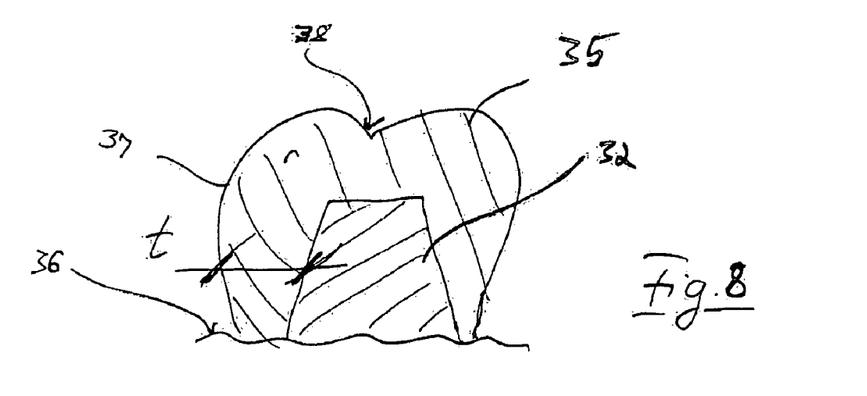
FIG. 8 is a sectional view of a restored tooth consisting of a basic structure and a crown.

Referring now to FIG. 8, the construction unit 30 determines the thickness t of the restoration body 35 represented by this dataset in an area that is relevant to the appearance of the denture. Preferably, this is an area 37 on the buccal or on the labial face of the tooth to be reconstructed that is located between the level of the gingiva 36 and the level of the occlusal surface 38 of the restoration body 35 to be constructed. Typically, the area 37 will be in the middle ⅓ of the tooth. However, depending upon the restoration being performed, the location 37 may be altered in special circumstances to achieve a desired match.

Using the data related to the relevant optical properties of the basic structure 32, such as the color and/or the translucency of the adjacent teeth 34 and the thickness t, the blank 51-53 of dental restoration material that best matches the desired appearance of the restoration body 25 when applied to the basic dental structure 32 can be determined. This is preferably done using the construction unit 30. Thus, a dependency between relevant optical properties of the basic dental structure 32, values of the relevant optical properties of the desired appearance, a thickness of the restoration body 35 and the relevant optical properties of different translucent dental materials is preferably stored in the storage area of the construction unit 30. The dependency may be stored as a functional dependency or as an empirically determined dependency in the form of a lookup table.

Figure 9:
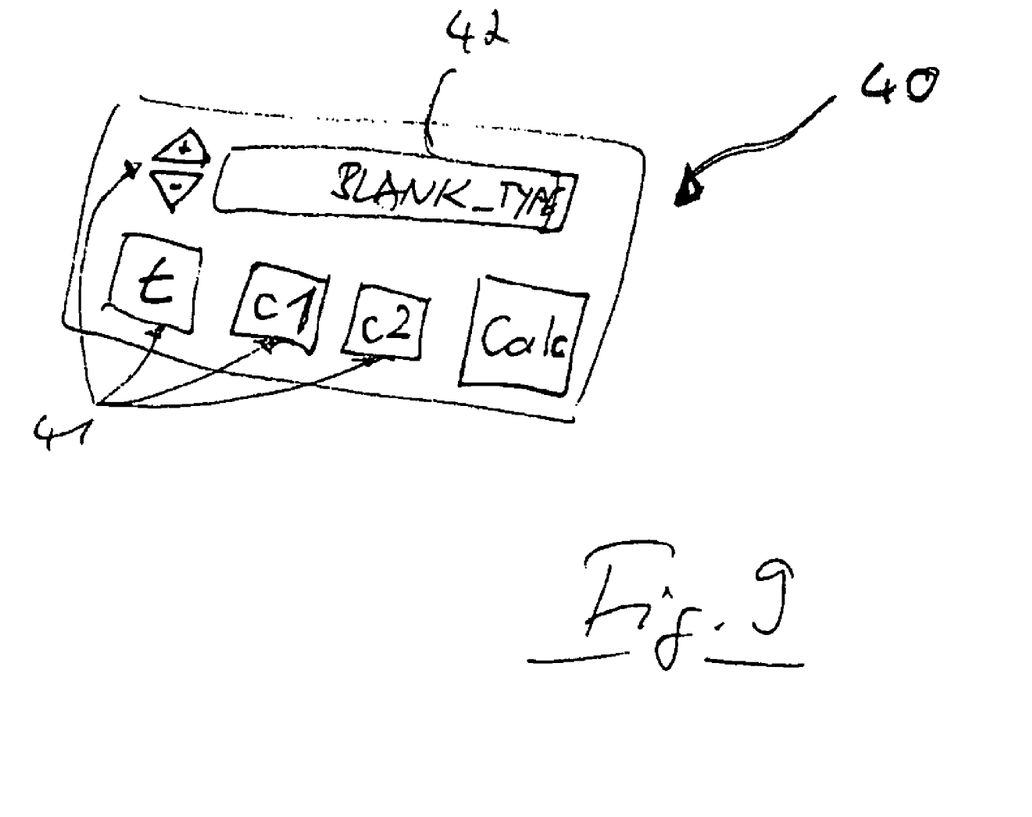
FIG. 9 is a schematic view of an apparatus for determining a translucent dental material.

Referring to now FIG. 9, a calculation unit 40 is shown which comprises input means for determining an appropriate blank 51-53 of translucent dental material. The calculation unit 40 comprises input buttons 41 for entering the relevant data necessary for determining the dental materials as discussed above. This data preferably includes the thickness t, a first optical value, c1, of the basic structure and a second optical value, c2, of the target appearance. Instead of entering actual numbers, initial values can be proposed and the values modified values with up and down buttons 41. After the data has been entered, the calculation unit 40 displays the appropriate blank type on a display 42. The input values are preferably stored in a first storage and the dependency of the input values stored in a second storage. However, it will be appreciated by those skilled in the art that the first and the second storage area can be part of a single storage area or memory since it is only a functional description of the storage area. An independent calculation unit 40 as discussed with respect to FIG. 9 is especially useful for upgrading pre-existing CAD/CAM units that have no ability to measure the desired optical properties.

The invention described herein addresses a heretofore unresolved problem of predicting the influence of a prepared tooth structure on the final shade of dental restorations when an opaque layer of material is not used. It does so in a manner that is both useful and efficient.

Thus, although there have been described particular embodiments of the present invention of a new and useful Method and Apparatus for Determining the Dental Material(s) that Will Result in the Correct Final Color of a Non-Opacious Dental Restoration by Measuring and Predicting the Influence of the Color of Prepared Teeth on the Final Color, it is not intended that such references be construed as limitations upon the scope of this invention except as set forth in the following claims.

What is claimed is:

1. A dental CAD/CAM system, said system comprising:
   a three dimensional measuring camera for measuring a three-dimensional shape of a basic dental structure;
   a measuring camera with an optical sensor for measuring relevant optical properties of said basic dental structure and relevant optical properties of a desired appearance;
   a dental restoration body construction unit having instructions effective to generate a dataset, said dataset further comprising
      a desired shape of a dental restoration body to be constructed in association with the measured three dimensional shape of the basic dental structure and
      a thickness of said dental restoration body for at least one area that is representative of an appearance of said dental restoration body applied on said basic dental structure;
   a first data storage area storing reference data of relevant optical properties of different translucent dental materials;
   a second data storage area storing data concerning a dependency between relevant optical properties of said basic dental structure, values of said relevant optical properties of the desired appearance, said thickness of said restoration body and relevant optical properties of said translucent dental materials,
   an interface for receiving target values of said desired appearance of said restoration body, said optical properties of said basic dental structure and said thickness of said restoration body; and
   a calculation unit effective to determine an appropriate translucent dental material for use in said dental restoration body based upon said reference data and said dependency.

2. An apparatus as defined in claim 1, wherein said optical sensor is an image detecting sensor.

3. An apparatus as defined in claim 1, wherein said measuring camera for measuring the relevant optical properties is the three dimensional measuring camera.

4. A method for producing a dental restoration body for application to a basic dental structure, said restoration body being made of a translucent dental material, wherein said method is a part of a CAD/CAM-process and said method comprises the steps of:
   providing a dataset concerning said dental restoration body for application to the basic dental structure using computer aided designs methods;
   providing reference data concerning relevant optical properties of different translucent dental materials and a dependency between relevant optical properties of said basic dental structure and said translucent dental materials, target values for desired optical properties of said dental restoration body to be produced, thickness of said restoration body and said relevant optical properties of said translucent dental material;
   determining said relevant optical properties of said basic dental structure;
   determining a target value corresponding to said desired optical properties of said restoration body when applied to said basic dental structure to be produced;
   determining a thickness of said dental restoration body to be produced on at least one area of said basic dental structure which is relevant for the appearance of said dental restoration body; and
   selecting a dental material for said dental restoration body based upon said reference data and said dependency between said optical properties of said basic dental structure and said translucent dental materials.

5. The method of claim 4 wherein said relevant optical properties of said different translucent dental materials comprise different color values or different translucency values.

6. The method of claim 5 wherein a color value for said target value is selected based upon optical properties of adjacent teeth of said basic dental structure.

7. The method of claim 5 wherein said translucency value is selected based upon optical properties of adjacent teeth of said basic dental structure.

8. The method of claim 4 wherein said basic dental structure is a prepared tooth.

9. The method of claim 4 wherein said dental restoration body is an inlay, an onlay, a crown or a veneer.

10. The method of claim 4 wherein said dependency is a functional dependency or an empirical known dependency.

11. A computer program for determining an appropriate translucent dental material or construction for use in producing a dental restoration for use with an existing dental structure, said computer program comprising:

a data base containing optical properties of different translucent dental materials or constructions and a dependency between optical properties of said dental restoration, said existing dental structure and said translucent dental materials or constructions;

an input routine effective to receive information, said information comprising a desired optical property and thickness of said dental restoration to be produced, said thickness representative of an area relevant to an appearance of the dental structure in use with the existing dental structure; and a selection routine effective to determine an appropriate dental material or construction for use in producing said dental restoration based upon a relationship between said desired optical property and thickness of said dental restoration, said optical properties of said existing dental structure and said translucent dental material or construction.

12. The computer program of claim 11 wherein said computer program is incorporated in a shade determination device.

13. The computer program of claim 11 wherein said computer program is incorporated in a dental CAD/CAM system.

14. The computer program of claim 11 wherein said relationship is a functional dependency or an empirical known dependency contained in a look-up table.

15. The computer program of claim 11 wherein said existing dental structure is a prepared tooth.

16. The computer program of claim 11 wherein said dental restoration body is an inlay, an onlay, a crown or a veneer.

17. The computer program of claim 11 wherein said desired optical property further comprises a color value.

18. The computer program of claim 11 wherein said desired optical property further comprises a translucency value.

19. The computer program of claim 11 wherein said desired optical property is based upon an optical property of adjacent teeth of said existing dental structure.

20. The computer program of claim 19 wherein said optical property of adjacent teeth of said existing dental structure is obtained from a camera measuring said adjacent teeth with as optical sensor.

* * * * *

UNITED STATES PATENT AND TRADEMARK OFFICE
CERTIFICATE OF CORRECTION

PATENT NO. : 7,623,942 B2
APPLICATION NO. : 11/327288
DATED : November 24, 2009
INVENTOR(S) : C. Alex Touchstone It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 992 days.

Signed and Sealed this

Twenty-sixth Day of October, 2010

David J. Kappos
*Director of the United States Patent and Trademark Office*